United States Patent [19]

Pfister et al.

[11] Patent Number: 5,081,270

[45] Date of Patent: Jan. 14, 1992

[54] PREPARATION OF HYDROXYANTHRAQUINONES

[75] Inventors: Juergen Pfister, Speyer; Michael Schiessl, Altrip; Rainer Nachtrab, Ludwigshafen, all of Fed. Rep. of Germany

[73] Assignee: BASF Aktiengesellschaft, Ludwigshafen, Fed. Rep. of Germany

[21] Appl. No.: 599,975

[22] Filed: Oct. 19, 1990

[30] Foreign Application Priority Data

Oct. 20, 1989 [DE] Fed. Rep. of Germany ....... 3934934

[51] Int. Cl.$^5$ .......................................... C09C 49/543
[52] U.S. Cl. .................................................. 552/262
[58] Field of Search .......................................... 552/262

[56] References Cited

U.S. PATENT DOCUMENTS 2,695,302  11/1954  Schneid et al. ................. 552/262
4,077,972  3/1978   Baurecht et al. .............. 260/314.5

FOREIGN PATENT DOCUMENTS 2432564  1/1976  Fed. Rep. of Germany.
2549372  5/1977  Fed. Rep. of Germany.
474487   2/1915  France.

OTHER PUBLICATIONS

Methoden der Organischen Chemie, vol. 7/3c, 1979, p. 97, E. Muller et al., "Hydroxy-Anthrachinone Durch Ringschlubreaktionen".
Berichte der Deutschen Chemischen Gesellschaft, 64, 1931, pp. 2003-2010, F. Mayer et al., "Des 1-Methyl-Anthrachinons".
Schneckenmaschinen in der Verfahrenstechnik, 1972, pp. 120 to 127, H. Herrmann, "3.3 Schneckenkneter".

*Primary Examiner*—C. Warren Ivy
*Assistant Examiner*—Raymond Covington
*Attorney, Agent, or Firm*—Oblon, Spivak, McClelland, Maier & Neustadt

[57] ABSTRACT

1-Hydroxyanthraquinones are prepared in an improved process by reacting phthalic anhydride or derivatives thereof with phenol derivatives in the presence of a Lewis acid as catalyst and in the presence or absence of a diluent, wherein the improvement comprises conducting the reaction in a self-cleaning apparatus having a mixing effect, at a temperature of from 120° C. to 300° C. for from 5 to 1,000 seconds, the self-cleaning apparatus having a mixing effect subjecting the reactants to a shear gradient of from 50 to 20,000 sec$^{-1}$ with an energy input of from 0.01 to 0.2 kwh/kg of reactants.

12 Claims, No Drawings

PREPARATION OF HYDROXYANTHRAQUINONES

The present invention relates to a novel process for preparing 1-hydroxyanthraquinones by reacting phthalic anhydride or derivatives thereof with phenol derivatives in the presence of a Lewis acid as catalyst and in the presence or absence of a diluent in a self-cleaning apparatus with a mixing effect.

It is known from Houben-Weyl, Methoden der Organischen Chemie, Volume 7/3c, page 97, and from Chem. Ber. 64 (1931), 2003-10, to react hydroquinone with 3-methylphthalic anhydride or with 3,6-dichlorophthalic anhydride in the presence of aluminum chloride as catalyst and sodium chloride as diluent to give the corresponding anthraquinones (1-methyl-5,8-dihydroxyanthraquinone or 5,8-dichloro-1,4-dihydroxyanthraquinone). The disadvantage with this type of reaction is the fact that the reaction mixture solidifies during the reaction and thus ceases to be stirrable. This procedure is therefore completely unsuitable for carrying out the reaction on an industrial scale. Another factor is that the workup of the solidified reaction mixture on an industrial scale presents serious problems.

It is an object of the present invention to provide a new process for preparing 1-hydroxyanthraquinones which likewise starts from phthalic anhydride or derivatives thereof and from phenol derivatives but with which the abovementioned difficulties are obviated and which also gives the target products in good yield and high purity within a short reaction time. In addition, the molar ratio between the reactants should ideally be equimolar.

We have found that this object is achieved by a process for preparing a hydroxyanthraquinone of the formula I

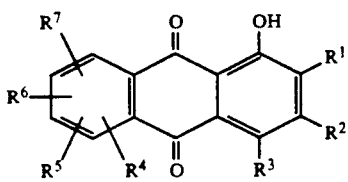

where
R$^1$ and R$^2$ are identical or different and each is independently of the other hydrogen, hydroxyl, C$_1$-C$_4$-alkyl or halogen or R$^1$ and R$^2$ together are a fused benzene ring which may be substituted or a fused C$_5$-C$_7$-cycloalkyl ring which may likewise be substituted, R$^3$ is hydroxyl, amino or halogen and R$^4$, R$^5$, R$^6$ and R$^7$ are identical or different and each is independently of the others hydrogen, halogen, hydroxyl, C$_1$-C$_4$-alkyl or C$_1$-C$_5$-alkanoyl, by reacting a phthalic anhydride of the formula II

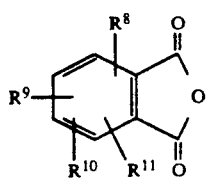

where

R$^8$, R$^9$, R$^{10}$ and R$^{11}$ are identical or different and each is independently of the others hydrogen, halogen, C$_1$-C$_4$-alkyl, C$_1$-C$_5$-alkanoyl, C$_1$-C$_4$-alkoxy, C$_1$-C$_5$-alkanoyloxy or sulfato, with a phenol derivative of the formula III

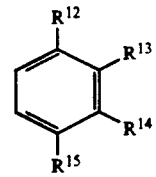

where

R$^{12}$ is hydroxyl, C$_1$-C$_4$-alkoxy, C$_1$-C$_5$-alkanoyloxy or sulfato,

R$^{13}$ and R$^{14}$ are identical or different and each is independently of the other hydrogen, hydroxyl, C$_1$-C$_4$-alkoxy, C$_1$-C$_5$-alkanoyloxy, C$_1$-C$_4$-alkyl, halogen or sulfato or R$^{13}$ and R$^{14}$ are together a fused benzene ring which may be substituted or a fused C$_5$-C$_7$-cycloalkyl ring which may likewise be substituted, and R$^{15}$ is hydroxyl, C$_1$-C$_4$-alkoxy, C$_1$-C$_5$-alkanoyloxy, sulfato, halogen or mono- or di(C$_1$-C$_5$-alkanoyl)-amino, in the presence of a Lewis acid as catalyst and in the presence or absence of a diluent in a self-cleaning apparatus having a mixing effect.

Any alkyl appearing in the abovementioned formulae may be either straight-chain or branched.

If R$^1$ and R$^2$ in the formula I together are a fused benzene ring which may be substituted or a fused C$_5$-C$_7$-cycloalkyl ring which may likewise be substituted, possible substituents are for example C$_1$-C$_4$-alkyl, C$_1$-C$_4$-alkoxy and halogen, the last being in particular chlorine or bromine.

If R$^1$ and R$^2$ together are a fused C$_5$-C$_7$-cycloalkyl ring, said ring may be for example a cyclopentyl, cyclohexyl or cycloheptyl ring. These rings may also be further substituted as mentioned above.

R$^1$, R$^2$, R$^4$, R$^5$, R$^6$, R$^7$, R$^8$, R$^9$, R$^{10}$, R$^{11}$, R$^{13}$ and R$^{14}$ are each for example methyl, ethyl, propyl, isopropyl, butyl, isobutyl or sec-butyl.

R$^4$, R$^5$, R$^6$, R$^7$, R$^8$, R$^9$, R$^{10}$, R$^{11}$, R$^{13}$ and R$^{14}$ may each also be for example fluorine, chlorine or bromine, which also applies to R$^3$ and R$^{15}$.

R$^4$, R$^5$, R$^6$, R$^7$, R$^8$, R$^9$, R$^{10}$ and R$^{14}$ may each also be for example formyl, acetyl, propionyl, butyryl, isobutyryl or pentanoyl.

R$^8$, R$^9$, R$^{10}$, R$^{11}$, R$^{13}$, R$^{14}$ and R$^{15}$ may each also be for example methoxy, ethoxy, propoxy, isopropoxy, butoxy, isobutoxy, sec-butoxy, formyloxy, acetyloxy, propionyloxy, butyryloxy, isobutyryloxy or pentanoyloxy, which also applies to R$^{12}$.

R$^{15}$ may also be for example mono- or diformylamino, mono- or diacetylamino or mono- or dipropionylamino.

Preference is given to reacting phthalic anhydrides of the formula II where R$^8$, R$^9$, R$^{10}$ and R$^{11}$ are identical or different and each is independently of the others hydrogen or chlorine with phenol derivatives of the formula III where R$^{12}$ is hydroxyl, C$_1$-C$_4$-alkoxy or C$_1$-C$_5$-alkanoyloxy, R$^{13}$ and R$^{14}$ are each hydrogen and R$^{15}$ is hydroxyl, C$_1$-C$_4$-alkoxy, C$_1$-C$_5$-alkanoyloxy or chlorine.

Particular preference is given to reacting an unsubstituted phthalic anhydride with hydroquinone. The product obtained in this case is quinizarine (1,4-di-hydroxyanthraquinone).

The process according to the present invention is carried out in the presence of a Lewis acid. Lewis acids which are suitable for the novel process are for example boron trifluoride, aluminum chloride, aluminum bromide, tin(IV) chloride, antimony(III) chloride, antimony(III) bromide, antimony(V) chloride, zinc chloride, mercury(II) chloride, mercury(II) bromide, titanium(IV) chloride, titanium(IV) bromide, molybdenum-(IV) bromide, iron(III) chloride and iron(III) bromide.

Preference is given to aluminum chloride, aluminum bromide or mixtures of aluminum chloride or aluminum bromide with catalytic amounts of boron trifluoride or iron(III) chloride.

The use of aluminum chloride as Lewis acid must be particularly emphasized.

In some cases it can also be of advantage to carry out the novel process in the additional presence of small amounts of boric acid.

The process according to the present invention can be carried out not only in the presence but also in the absence of a diluent, the former case being preferred.

Suitable diluents are for example salts, in particular alkali metal or alkaline earth metal halides or ammonium halides, such as lithium chloride, lithium bromide, sodium chloride, sodium bromide, magnesium chloride, magnesium bromide, calcium chloride, calcium bromide, ammonium chloride, ammonium bromide and mixtures thereof.

Preference is given to the use of sodium chloride, potassium chloride, ammonium chloride or mixtures thereof.

Particular preference is given to the use of sodium chloride, potassium chloride or mixtures thereof, the use of sodium chloride being particularly important.

In general, from 0.25 to 0.80 mol of diluent is used per mole of Lewis acid.

Favorable results are obtained with the simultaneous use of aluminum chloride as Lewis acid and sodium chloride, potassium chloride or mixtures thereof as diluent. It is advantageous to use these components in a molar ratio of aluminum chloride:sodium chloride or potassium chloride of from 1.3:1 to 4:1, preferably from 1.7:1 to 2.2:1, or in a molar ratio of aluminum chloride:sodium chloride:potassium chloride of from 3:1.25:1 to 11.5:1.75:1, preferably from 3.7:1.35:1 to 5.4:1.45:1.

The molar ratio of phthalic anhydride II:phenol derivative III is customarily from 1:1 to 10:1, preferably from 1:1 to 2.5:1.

In general, from 2 to 10 mol, preferably from 2 to 3 mol, of Lewis acid are used per mole of phenol derivative III.

The process according to the present invention is carried out in a self-cleaning apparatus having a mixing effect. Apparatus of this type is known per se and is commercially available. Suitable reactors of this type are for example the chamber reactor, the recycle reactor and the screw reactor, preference being given to carrying out the process according to the present invention in the screw reactor.

Particular emphasis must be given here to the use of a cocurrent, intermeshing twin-shaft screw kneader as described for example in H. Herrmann, Schneckenmaschinen in der Verfahrenstechnik, pages 120 to 127, Springer Verlag, Berlin, 1972. Such a screw kneader has kneading disks as mixing and kneading elements and possesses a self-cleaning seal profile.

The novel process may be carried out batchwise but is preferably carried out as a continuous process.

The reaction of the phthalic anhydride II with the phenol derivative III is in general carried out at atmospheric pressure and at from 120° to 300° C, preferably at from 180° to 250° C., in particular at from 220° to 240° C.

The reaction time, ie. the residence time in the self-cleaning, closely intermeshing apparatus with mixing effect, is customarily from 5 to 1,000 seconds, preferably from 10 to 600 seconds, in particular from 10 to 100 seconds, although particular emphasis must be given to the range from 10 to 70 seconds.

The shear gradient in the self-cleaning apparatus with mixing effect is customarily from 50 to 20,000 $\text{sec}^{-1}$, preferably from 250 to 3,500 $\text{sec}^{-1}$. The specific energy input during shearing is in general from 0.01 to 0.2 kWh/kg.

Since the reactants can be metered in not only in the solid but also in the liquid state, there are several possible ways of carrying out the process according to the present invention:

Phthalic anhydride II, phenol derivative III, Lewis acid and any diluent are added mixed or separately with all the components being in the solid state before being liquefied in the reactor in a melting zone.

Lewis acid and any diluent are introduced first, both as liquids. Phthalic anhydride II and phenol derivative III are added as a mixture in which both components are solids.

Lewis acid and any diluent are introduced first, both as liquids. Phthalic anhydride II and phenol derivative III are added as a mixture in which both components are likewise liquids.

Lewis acid and any diluent are introduced first, both as liquids. Phthalic anhydride II and phenol derivative III are added either at the same time but at different points or, alternatively, the phthalic anhydride II first and the phenol derivative III second, in which case phthalic anhydride II and phenol derivative III may each be in the liquid or solid state.

Once all the reactants have been metered into the reactor, they are heated to the abovementioned reaction temperature, unless they are already of course at that temperature as a result of liquefaction, and the formation of the target product then takes place.

After the reaction has ended, the reaction mixture is treated with an aqueous acid, and target product I is then separated off, washed and dried in a conventional manner.

The aqueous acid can be not only an aqueous inorganic acid, for example hydrochloric acid or dilute sulfuric acid, but also an aqueous organic acid, for example aqueous oxalic acid. The use of hydrochloric acid is preferred.

If the process according to the present invention is carried out with aluminum chloride as Lewis acid, it is advantageous to dissolve the hydrogen chloride released in the course of the reaction in water and to use the resulting hydrochloric acid as the aqueous acid.

The treatment with the aqueous acid can be carried out batchwise but is preferably carried out continuously.

The process according to the present invention is notable for a whole series of advantages. For instance, the reaction time, ie. the residence time in the reactor, is very short, which makes for a selective reaction. The target products are therefore obtained in high purity. Furthermore, the novel process has a favorable space-time yield. In addition, a high excess of one of the two reactants can be avoided; that is, the reactants are made to react in approximately stoichiometric ratio. Finally, no organic solvent is required.

The hydroxyanthraquinones of the formula I are useful intermediates for preparing anthraquinone dyes.

The Examples which follow further illustrate the invention.

EXAMPLE 1

A twin-shaft screw kneader of the type ZSK (from Werner und Pfleiderer, Stuttgart) whose internal temperature was 230° C. was continuously charged at a rate of 5 kg/h with a mixture of 0.71 kg (6.45 mol) of hydroquinone, 1.20 kg (8.10 mol) of phthalic anhydride, 2.58 kg (19.35 mol) of aluminum chloride and 0.51 kg (8.73 mol) of sodium chloride (each in the solid state). The mixture formed a melt and began to react. The gaseous hydrogen chloride formed in the course of the reaction at a rate of 450 l/h was conducted out of the reactor. The residence time in the reactor was 40 seconds. The resulting aluminum complex (4.3 kg/h) was hydrolyzed at 80° C. with 12.9 kg of 10% strength by weight hydrochloric acid for 30 minutes. The target product (1,4-dihydroxyanthraquinone) was filtered off with suction on a filter press, washed neutral with 70 l of water and dried. Yield: 1.0 kg/h (yield: 65%; purity: >95%).

The same method was used to carry out the Examples listed below in Table 1, where the following abbreviations apply:

HQ = hydroquinone
PA = phthalic anhydride.

TABLE 1

| Example No. | PA:HQ | Molar ratio AlCl$_3$:HQ | AlCl$_3$:NaCl | Temperature | Residence time | Yield | Purity | 10% strength by weight hydrochloric acid per mole of HQ |
|---|---|---|---|---|---|---|---|---|
| 2 | 1.2:1 | 3.0:1 | 2.2:1 | 280° C. | 40 sec | 82% | 90% | 1.5 kg |
| 3 | 1.2:1 | 3.0:1 | 2.2:1 | 230° C. | 80 sec | 65% | >95% | 1.5 kg |
| 4 | 1.2:1 | 5.0:1 | 2.2:1 | 230° C. | 40 sec | 80% | >95% | 2.0 kg |

In the Examples listed below in Table 2, in each case a mixture of aluminum chloride and sodium chloride (in the liquid state) was introduced into a screw reactor (as described in Example 1), and phthalic anhydride and hydroquinone (both likewise in the liquid state) were metered in at the same time but at separate points.

TABLE 2

| Example No. | PA:HQ | Molar ratio AlCl$_3$:HQ | AlCl$_3$:NaCl | Temperature | Residence time | Yield | Purity | 10% strength by weight hydrochloric acid per mole of HQ |
|---|---|---|---|---|---|---|---|---|
| 5 | 1.2:1 | 3.0:1 | 2.2:1 | 230° C. | 40 sec | 90% | >95% | 2.0 kg |
| 6 | 1.2:1 | 3.0:1 | * | 230° C. | 40 sec | 90% | >95% | 2.0 kg |
| 7** | 1.2:1 | 3.0:1 | 2.2:1 | 230° C. | 40 sec | 90% | >95% | 2.0 kg |
| 8*** | 1.2:1 | 3.0:1 | 2.2:1 | 230° C. | 40 sec | 85% | >95% | 2.0 kg |

*Instead of sodium chloride a mixture of sodium chloride and potassium chloride was used. The molar ratio of AlCl$_3$:NaCl:KCl was 5.4:1.45:1.
**Hydroquinone dimethyl ether was used instead of hydroquinone.
***Hydroquinone diacetate was used instead of hydroquinone.

EXAMPLE 9

Example 9 was carried out in the same way as Example 5 except that the hydroquinone was replaced by 4-chlorophenol. The yield of 1-chloro-4-hydroxyanthraquinone was 90% (purity >95%).

EXAMPLE 10

Example 10 was carried out in the same way as Example 1 except that the phthalic anhydride was replaced by 1,2,3,4-tetrachlorophthalic anhydride. From the residence time in the reactor of 80 sec the yield of 1,2,3,4-tetrachloro-6,9-dihydroxyanthraquinone was 92% (melting point 240° C. (with decomposition)).

$C_{14}H_4Cl_4O_4$ (378) calculated C 44.4, H 1.1, O 16.9, Cl 37.6, found C 43.8, H 1.0, O 17.1, Cl 37.8.

$^{13}$C NMR ([D$_6$]DMSO):δ = 113.5 (s; C-8a, C-5a), 129.0 (d; C-6, C-7), 131.5 (s; C-1, C-4), 132.3 (s; C-1a, C-4a), 139.7 (s; C-2, C-3), 155 (s; C-5, C-8), 183.5 ppm (s; C-9, C-10).

We claim:

1. In a process for preparing a hydroxyanthraquinone of the formula I where

R$^1$ and R$^2$ are identical or different and each is independently of the other hydrogen, hydroxyl, C$_1$-C$_4$-alkyl or halogen, or R$^1$ and R$^2$ together are a fused benzene ring which may be substituted or a fused C$_5$-C$_7$-cycloalkyl ring which may likewise be substituted, R$^3$ is hydroxyl, amino or halogen and R$^4$, R$^5$, R$^6$ and R$^7$ are identical or different and each is independently of the others hydrogen, halogen, hydroxyl, C$_1$-C$_4$-alkyl or C$_1$-C$_5$-alkanoyl, by reacting a phthalic anhydride of the formula II

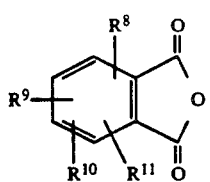

(II)

where
$R^8$, $R^9$, $R^{10}$ and $R^{11}$ are identical or different and each is independently of the others hydrogen, halogen, $C_1-C_4$-alkyl, $C_1-C_5$-alkanoyl, $C_1-C_4$-alkoxy, $C_1-C_5$-alkanoyloxy or sulfato, with a phenol derivative of the formula III

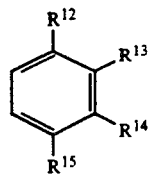

(III):

where
$R^{12}$ is hydroxyl, $C_1-C_4$-alkoxy, $C_1-C_5$-alkanoyloxy or sulfato,
$R^{13}$ and $R^{14}$ are identical or different and each is independently of the other hydrogen, hydroxyl, $C_1-C_4$alkoxy, $C_1-C_5$-alkanoyloxy, $C_1-C_4$-alkyl, halogen or sulfator, or $R^{13}$ and $R^{14}$ are together a fused benzene ring which may be substituted or a fused $C_5-C_7$-cycloalkyl ring which may likewise be substituted, and
$R^{15}$ is hydroxyl, $C_1-C_4$-alkoxy, $C_1-C_5$-alkanoyloxy, sulfator, halogen or mono- or di-($C_1-C_5$-alkanoyl)-amino, in the presence of a Lewis acid as catalyst, the improvement comprising conducting said reaction in a self-cleaning apparatus having a mixing effect, at a temperature of from 120° to 300° C. for from 5 to 1,000 seconds, said self-cleaning apparatus having a mixing effect subjecting said reactants to a shear gradient of from 50 to 20,000 sec$^{-1}$ with an energy input of from 0.01 to 0.2 kwh/kg of reactants.

2. A process as claimed in claim 1, wherein a phthalic anhydride of the formula II where $R^8$, $R^9$, $R^{10}$ and $R^{11}$ are identical or different and each is independently of the others hydrogen or chlorine is reacted with a phenol derivative of the formula III where $R^{12}$ is hydroxyl, $C_1-C_4$-alkoxy or $C_1-C_5$-alkanoyloxy, $R^{13}$ and $R^{14}$ are each hydrogen and $R^{15}$ is hydroxyl, $C_1-C_4$-alkoxy, $C_1-C_5$-alkanoyloxy or chlorine.

3. A process as claimed in claim 1, wherein the Lewis acid used is aluminum chloride, aluminum bromide or a mixture of aluminum chloride or aluminum bromide with boron trifluoride or iron(III) chloride.

4. A process as claimed in claim 1, wherein the reaction is carried out in the presence of a diluent.

5. A process as claimed in claim 4, wherein the diluent used is sodium chloride, potassium chloride, ammonium chloride or a mixture thereof.

6. A process as claimed in claim 1, wherein said temperature is from 180° to 250° C.

7. A process as claimed in claim 1, wherein said temperature is from 220° to 240° C.

8. A process as claimed in claim 1, wherein said reaction time is from 10 to 600 seconds.

9. A process as claimed in claim 1, wherein said reaction time is from 10 to 100 seconds.

10. A process as claimed in claim 1, wherein said reaction time is from 10 to 70 seconds.

11. A process as claimed in claim 1, wherein said shear gradient is from 250 to 3,500 sec$^{-1}$.

12. A process as claimed in claim 1, wherein said process is carried out continuously.

* * * * *